United States Patent [19]

Makryaleas et al.

[11] Patent Number: 5,405,761

[45] Date of Patent: Apr. 11, 1995

[54] METHOD FOR THE PREPARATION OF SALTS OF L-ORNITHINE

[75] Inventors: Kyriakos Makryaleas; Karlheinz Drauz, both of Freigericht, Germany

[73] Assignee: Degussa Aktiengesellschaft, Frankfurt am Main, Germany

[21] Appl. No.: 715,963

[22] Filed: Jun. 17, 1991

[30] Foreign Application Priority Data

Jul. 2, 1990 [DE] Germany .................. 40 20 980.6

[51] Int. Cl.$^6$ ............................................. C12P 13/10
[52] U.S. Cl. .................................... 435/114; 435/227
[58] Field of Search ................ 435/114, 227; 562/554, 562/560

[56] References Cited

U.S. PATENT DOCUMENTS

| | | | |
|---|---|---|---|
| 3,222,258 | 12/1965 | Iizuka et al. | 435/114 |
| 3,668,072 | 6/1972 | Ando et al. | 435/114 |
| 4,248,677 | 2/1981 | Kato | 562/560 |
| 4,346,169 | 8/1982 | Akashi et al. | 435/114 |
| 4,420,432 | 12/1983 | Chibata et al. | 562/560 |
| 4,698,442 | 10/1987 | Nestor et al. | 562/560 |
| 5,059,712 | 10/1991 | Griffith | 514/565 |

*Primary Examiner*—Marian Knode
*Attorney, Agent, or Firm*—Cushman, Darby & Cushman

[57] ABSTRACT

Salts of L-ornithine are prepared by means of the enzymatic conversion of arginine to L-ornithine in the presence of the enzyme L-arginase in an aqueous medium in such a manner that the acid whose salt is to be prepared is used for the adjustment of the pH for the enzymatic conversion and for the subsequent neutralization of the reaction mixture and that the salt formed is isolated directly from the reaction mixture.

2 Claims, No Drawings

METHOD FOR THE PREPARATION OF SALTS OF L-ORNITHINE

The present invention relates to a method for the preparation of salts of L-ornithine by means of the enzymatic conversion of arginine into L-ornithine in the presence of the enzyme L-arginase (E.C.3.5.3.) in an aqueous medium and by means of a subsequent formation of the salt.

BACKGROUND OF THE INVENTION

Salts of L-ornithine are valuable pharmaceutical products which are useful, e.g., for parenteral nutrition (L-ornithine acetate or L-ornithine monohydrochloride) and the treatment of hepatic diseases (L-ornithine aspartate or L-ornithine-2-ketoglutarate).

SUMMARY OF THE INVENTION

The present invention provides a method for the enzymatic conversion of arginine into L-ornithine in the presence of the enzyme L-arginase (E.C.3.5.3.1) in an aqueous medium in which the pH required for the enzymatic conversion is maintained in a range of 8.0 to 10.0 with the acid whose salt is to be prepared, the pH is adjusted to the range 6.5 to 7.0 after the end of the enzymatic conversion with the same acid and the salt formed is isolated directly from the reaction mixture.

It is especially advantageous if the enzyme is separated from the reaction mixture by ultrafiltration before the isolation of the salt formed.

During the practical operation of the method of the invention, the original pH of the aqueous arginine solution of approximately 11.0 is first adjusted with the acid whose salt is to be prepared to a pH in a range of 8.0 to 10.0. Then, it is advantageous to add a slight amount of a salt of a bivalent metal in order to achieve a high activity of the enzyme. An addition of $Mn^{2+}$ salts in a $10^{-3}$ to $10^{-5}$ molar concentration is especially suitable. After the addition of the L-arginase, the enzymatic conversion is carried out at a temperature between 5° C. and 50° C., preferably between 20° C. and 35° C. The reaction time required is a function of the amount of enzyme used and is generally between 5 and 48 hours.

The arginine is advantageously used in a concentration of 5 to 40% by weight, preferably in the L form. It can also be used in the D,L form; however, the non-reacted D-arginine must then be separated after the end of the enzymatic conversion and prior to the neutralization of the reaction mixture from the L-ornithine which has formed. This can take place e.g. by means of ion exchange chromatography.

The L-arginase is isolated from animal liver and can be used both in its natural form as well as in a suitable stabilized form. It is commercially available in both forms.

After end of the enzymatic conversion and, if necessary, after separation of the non-reacted D-arginine, the reaction mixture is adjusted, that is neutralized, with the acid whose salt is to be prepared to a pH in a range of 6.5 to 7.0.

The desired salt of L-ornithine can then be isolated directly from the reaction mixture, e.g. by means of concentration by evaporation until crystallization or by means of precipitation with an organic solvent miscible with water, preferably with methanol or especially ethanol.

Practically any salts of L-ornithine can be prepared by means of the method of the invention. They can be the salts of inorganic acids such as hydrochloric acid, sulfuric acid or phosphoric acid. However, the method of the invention is especially suited for the preparation of the salts of L-ornithine with organic acids. Suitable organic acids are e.g. saturated aliphatic monocarboxylic acids such as formic acid, acetic acid or propionic acid; unsaturated aliphatic monocarboxylic acids such as oleic acid, linoleic acid or linolenic acid; functionalized acids such as hydroxycarboxylic acids (e.g. lactic acid or mandelic acid), ketocarboxylic acids (e.g. α-ketoglutaric acid), amino carboxylic acids (e.g. aspartic acid, glutamic acid or pyroglutamic acid); saturated aliphatic dicarboxylic acids such as succinic acid or adipic acid; unsaturated aliphatic dicarboxylic acids such as maleic acid or fumaric acid; aromatic carboxylic acids such as salicylic acid; araliphatic carboxylic acids such as phenylacetic acid, phenylpropionic acid or cinnamic acid; or functionalized di- and tricarboxylic acids such as malic acid or citric acid.

Surprisingly, no inhibition or deactivation of the enzyme occurs when using the very varied acids for adjusting the pH necessary for the enzymatic conversion. As a consequence, the very varied salts of L-ornithine can be prepared in a simple manner and in high yield in accordance with the method of the invention.

DETAILED DESCRIPTION OF PREFERRED EMBODIMENTS

The method of the invention is illustrated in more detail by the following examples. The course of the enzymatic conversion can be followed via the determination of the L-ornithine formed or of the L-arginine consumed by means of chromatography. The formed salts are characterized by the specific rotation and by elementary analysis.

EXAMPLE 1

130.5 g L-arginine were stirred into 800 ml $H_2O$ and adjusted with α-ketoglutaric acid to pH=9.5. After the addition of 0.042 g $MnSO_4.H_2O$, the reactor was filled to 1,000 ml with $H_2O$. After the addition of 220 mg arginase, the reaction mixture was agitated 20 hours at room temperature.

Thereafter, the solution was neutralized with α-ketoglutaric acid and ultrafiltered for the purpose of enzyme separation, concentrated by evaporation in a rotary evaporator and compounded under cooling with ethanol, at which time the product crystallized out. With 166.6 g isolated (di-L-ornithine)-α-ketoglutarate dihydrate, the yield was 97%, relative to the L-arginine used. The isolated product had the following properties:

Content (titration): >99%

Specific rotation: $[\alpha]\ 20_D = +7.8°(c=5$ in $H_2O)$

|  | Elementary analysis: | | |
| --- | --- | --- | --- |
|  | % C | % H | % N |
| Calculated: | 40.3 | 7.6 | 12.55 |
| Observed: | 39.13 | 8.08 | 14.06 |
| Drying loss: | 9.9% | | |
| Sulfate ash: | <0.1% | | |

EXAMPLE 2

The same method was used as in Example 1; however, 174.3 L-arginine were added and L-asparatic acid was used to adjust the reaction pH and to neutralize the generated L-ornithine.

The isolated yield of L-ornithine-L-aspartate was 99% relative to L-arginine used. The isolated product had the following properties:
Content (titration): >99%
Specific rotation $[\alpha] 20_D = +28.0°$ (c=8 in 6N HCl)

| | D Elementary analysis: | | |
|---|---|---|---|
| | % C | % H | % N |
| Calculated: | 40.71 | 7.31 | 15.83 |
| Observed: | 37.93 | 8.23 | 15.38 |
| Drying loss: | 0.3% | | |

EXAMPLE 3

The same method was used as in Example 1; however, 348.5 g L-arginine were added and L-glutamic acid was used adjust the reaction pH and to neutralize the generated L-ornithine.

The isolated yield of L-ornithine-L-glutamate was 96.6% relative to L-arginine used. The isolated product had the following properties:
Content (titration): >99%
Specific rotation $[\alpha] 20_D = +30.4°$ (c=8 in 6N HCl)

| | Elemental analysis: | | |
|---|---|---|---|
| | % C | % H | % N |
| Calculated: | 42.99 | 7.52 | 15.04 |
| Observed: | 42.50 | 8.05 | 14.71 |
| Drying loss: | 0.7% | | |

EXAMPLE 4

The same method was used as in Example 1; however, L-pyroglutamic acid was used to adjust the reaction pH and to neutralize the generated L-ornithine. The isolated yield of L-ornithine-L-pyroglutamate monohydrate was 95.8% relative to L-arginine used. The isolated product had the following properties:
Content (titration): >99%
Specific rotation $[\alpha] 20_D = +17.2°$ (c=8 in 6N HCl)

| | Elementary analysis: | | |
|---|---|---|---|
| | % C | % H | % N |
| Calculated: | 43.1 | 7.52 | 15.05 |
| Observed: | 43.45 | 8.07 | 15.08 |
| Drying loss: | 5.4% | | |

EXAMPLE 5

The same method was used as in Example 1; however, $H_2SO_4$ was used to adjust the reaction pH and to neutralize the generated L-ornithine. The isolated yield of (L-ornithine)$_2$-sulfate monohydrate was 93.9% relative to L-arginine used. The isolated product had the following properties:
Content (titration): >99%
Specific rotation $[\alpha] 20_D = +8.2°$ (c=10 in $H_2O$)

| | Elementary analysis: | | |
|---|---|---|---|
| | % C | % H | % N |
| Calculated: | 31.57 | 7.4 | 14.73 |
| Observed: | 31.68 | 8.20 | 14.55 |
| Drying loss: | 4.4% | | |
| Sulfate ash: | 0.1% | | |

EXAMPLE 6

The same method was used as in Example 1; however, HCl was used to adjust the reaction pH and to neutralize the generated L-ornithine. The isolated yield of L-ornithine monohydrochloride was 97.4% relative to L-arginine used. The isolated product had the following properties:
Content (titration): >99%
Specific rotation $[\alpha] 20_D = +23.8°$ (c=4 in 6N HCl)

| | Elementary analysis: | | |
|---|---|---|---|
| | % C | % H | % N |
| Calculated: | 35.58 | 7.71 | 16.6 |
| Observed: | 35.40 | 8.38 | 14.31 |

EXAMPLE 7

The same method was used as in Example 1; however, acetic acid was used to adjust the reaction pH and to neutralize the generated L-ornithine. The isolated yield of L-ornithine acetate was 95.4% relative to L-arginine used. The isolated product had the following properties:
Content (titration): >99%
Specific rotation $[\alpha] 20_D = +10.0°$ (c=5 in $H_2O$)

EXAMPLE 8

The same method was used as in Example 1; however, D-mandelic acid was used to adjust the reaction pH and to neutralize the generated L-ornithine. The isolated yield of L-ornithine-D-mandelate dihydrate was 94.2% relative to L-arginine used. The isolated product had the following properties:
Content (titration): >99%
Specific rotation $[\alpha] 20_D = -52.7°$ (c=2 in $H_2O$)

| | Elementary analysis: | | |
|---|---|---|---|
| | % C | % H | % N |
| Calculated: | 48.75 | 7.5 | 8.75 |
| Observed: | 49.50 | 7.7 | 8.85 |
| Drying loss: | 9.4% | | |

EXAMPLE 9

The same method was used as in Example 1; however, phosphoric acid was used to adjust the reaction pH and to neutralize the generated L-ornithine. The isolated yield of (L-ornithine)$_3$-phosphate monohydrate was 93.1% relative to L-arginine used. The isolated product had the following properties:
Content (titration): >99%
Specific rotation $[\alpha] 20_D = +20.4°$ (c=8 in 6N HCl)

| Elementary analysis: | | | |
|---|---|---|---|
| | % C | % H | % N |
| Calculated: | 35.1 | 8.0 | 16.4 |
| Observed: | 30.19 | 7.47 | 14.7 |
| Drying loss: | 3.7% | | - |

EXAMPLE 10

The same method was used as in Example 1; however, glutathione in the form of the disulfide (GSSG) was used to adjust the reaction pH and to neutralize the generated L-ornithine. The isolated yield of (L-ornithine)$_2$-glutathione disulfide dihydrate was 97.7% relative to L-arginine used. The isolated product had the following properties:

Content (titration): >99%

Specific rotation $[\alpha]\,23_D32\ -70.3°$ (c=1.9 in H$_2$O)

| Elementary analysis: | | | |
|---|---|---|---|
| | % C | % H | % N |
| Calculated: | 38.4 | 6.14 | 14.34 |
| Observed: | 37.7 | 7.32 | 14.82 |
| Drying loss: | 5.4% | | |

What is claimed is:

1. A method for the preparation of salts of L-ornithine which comprises enzymatically converting arginine into L-ornithine in the presence of the enzyme L-arginase in an aqueous reaction medium and subsequently forming the salt; said process consisting of the steps of:
   a) adjusting a pH of said aqueous reaction medium to a range between 8.0 and 10.0 prior to the enzymatic process with an acid of the salt to be produced;
   b) maintaining the pH between 8.0 and 10.0 during the enzymatic conversion with the same acid as used in step (a);
   c) adjusting the pH of said aqueous reaction medium after said enzymatic conversion to a range between 6.5 and 7.0 with the same acid as used in step (a); and
   d) allowing the L-ornithine salt to crystalize from said aqueous reaction medium; and
   e) recovering the crystals formed.

2. A method as set forth in claim 1 further consisting of the step of removing the enzyme from the reaction mixture by ultrafiltration prior to the crystallization of the L-ornithine salt.

* * * * *